United States Patent [19]

Bar-Cohen et al.

[11] Patent Number: 4,457,174
[45] Date of Patent: Jul. 3, 1984

[54] ULTRASONIC INSPECTION OF COMPOSITE MATERIALS

[75] Inventors: Yoseph Bar-Cohen, Dayton, Robert L. Crane, Kettering, both of Ohio

[73] Assignees: Systems Research Laboratories Inc., Dayton, Ohio

[21] Appl. No.: 376,891

[22] Filed: May 10, 1982

[51] Int. Cl.$^3$ ............................................. G01N 29/04
[52] U.S. Cl. ....................................... 73/598; 73/620; 73/629; 73/633; 73/582
[58] Field of Search ................. 73/598, 610, 620, 624, 73/629, 633, 582

[56] References Cited

U.S. PATENT DOCUMENTS 3,813,926  6/1974  Stubbeman ............................ 73/629
4,008,602  2/1977  Love ..................................... 73/620

OTHER PUBLICATIONS

Rose, J. L. and Shelton, W., "Damage Analysis in Composite Materials," Composite Reliability, ASTM STP 580, American Society for Testing and Materials, 1975, pp. 215-226.

Hayford, D. T., Henneke, E. G., II, and Stinchcomb, W. W., "The Correlation of Ultrasonic Attenuation and Shear Strength in Graphite-Polyimide Composites," J. Composite Materials, vol. II, (Oct. 1977), pp. 429-444.

Hayford, D. T. and Henneke, E. G., II, "A Model for Correlating Damage and Ultrasonic Attenuation in Composites," Composite Materials: Testing and Design (Fifth Conference), ASTM STP 674, S. W. Tsai, Ed., American Society for Testing and Materials, 1979, pp. 184-200.

Primary Examiner—Howard A. Birmiel
Attorney, Agent, or Firm—Biebel, French & Nauman

[57] ABSTRACT

A method of ultrasonically inspecting the internal structure of a multi-ply composite material using ultrasonic transducers includes the steps of positioning an ultrasonic transmitter in acoustical contact with one surface of the material, directing a beam of acoustic energy into the material with the angle of incidence of the beam with respect to the surface being less than the second critical angle for the material but greater than normal to the surface, and receiving the reflected energy. In one embodiment, the transmitting and receiving transducers are positioned with their axis perpendicular to the orientation of the reinforcing fibers within the ply being inspected. In another embodiment, the transmitter and receiver are aligned at equal angles on either side of a line which is perpendicular to the orientation of the fibers. The receiver may be located on the same or the opposite side of the material from the transmitter. Internal cracks within each layer of the composite material can be detected along with information regarding their length and number. Further, by precessing the transducers, the orientation of the fibers within each ply will be revealed and this information may be used to confirm proper construction of the composite. Also, information regarding fiber overlap, wavyness and other characteristics of the composite with each ply can be ascertained.

13 Claims, 12 Drawing Figures

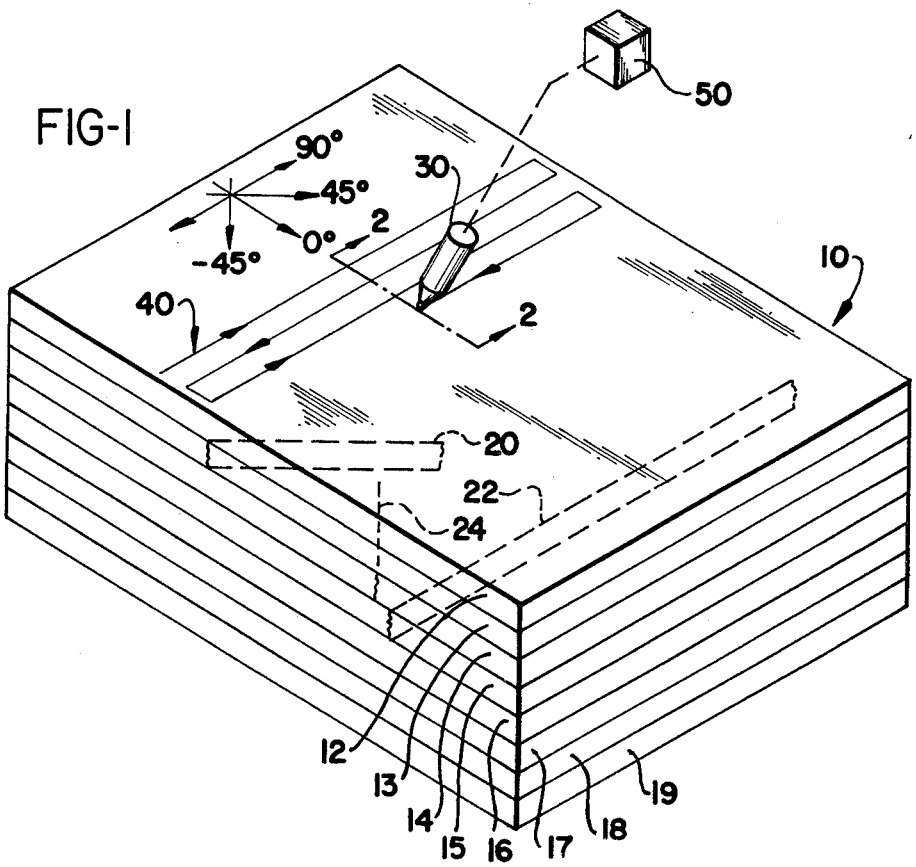
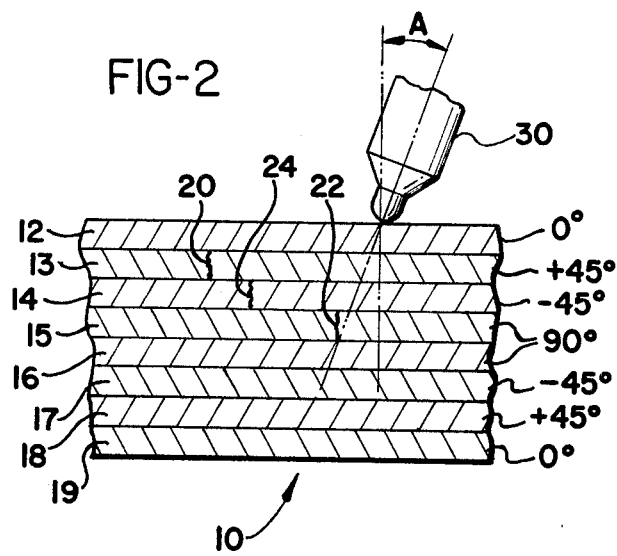

FIG-7
FIG-8
FIG-9a
$\theta = 0°$ 
FIG-9b
FIG-9 c

ULTRASONIC INSPECTION OF COMPOSITE MATERIALS

BACKGROUND OF THE INVENTION

This invention relates to a method for inspecting the internal structure of composite materials and particularly, a method for determining the length, number and position of cracks within each ply of a composite material, and also a method for determining the orientation of the fibers contained within each ply of the material.

This invention is particularly useful in inspecting composite materials used in aircraft structures. Since all aircraft are required to be capable of sustaining a specific amount of damage over a given time of unrepaired service, there is a need to track or monitor the actual amount of damage accumulated in flight critical components of the airframe structure.

With regard to metallic components, the inspection of actual damage is a relatively straightforward task involving monitoring the growth of surface connected cracks. With regard to composite structures, a different inspection or design approach was taken. Since the damage mechanism in composite materials is in the growth of a number or the density of small cracks within the high stress regions of the structure, and since these cracks lie between and beneath many layers or plys of the composite material, early non-destructive inspection methods were unavailable, and, therefore, aircraft designs using composite material were very conservative. Over time, confidence in the use of these material has grown, and the safety factors imposed on these materials have been significantly reduced. There is currently a renewed emphasis on a requirement to inspect the actual damage accumulation within composite materials in order to avoid the failure of critical components of an airframe structure and possible aircraft loss due to unexpected material failures.

One prior art technique for inspecting composite materials for cracks utilizes a radiographically opaque penetrant tetrebromo-ethane (TBE) to enhance the image of surface connected cracks on X-ray radiographs. This technique provides a clear indication of very small flaws; however, all of the flaws detected by this method must be surface connected in order for the penetrating fluid to find its way into the flaw, and also, TBE is toxic to humans and can cause stress-corrosion of aluminum structures. The usefulness of this technique is therefore limited, particularly, in operational aircraft where the cracks or flaws to be detected are almost always located beneath non-cracking surface layers.

A second defect or flaw detecting method uses an ultrasonic beam and attempts to determine or infer the presence and the number of small cracks within the material by the attenuation of a normally incident acoustic beam as it traverses the specimen under examination. With this method, however, the presence of a substantial number of small cracks has very little effect on the attenuation of an ultrasonic wave. Indeed, changes in surface roughness, volume fraction of reinforcing fibers, and the like, have a far larger effect on the measured attenuation of the acoustic wave than do numerous small flaws. Also, this technique does not provide any indication of the depth of the cracks within the structure or the orientation of these cracks or flaws.

SUMMARY OF THE INVENTION

This invention relates to a method of inspecting composite materials ultrasonically to detect not only the presence of flaws which are not necessarily surface connected, but the invention may also be used to determine the orientation of the fibers within each of the plys or layers which comprise the composite material.

A typical composite structure includes a plurality of layers of fiber-reinforced materials, with each layer being oriented with respect to a reference to provide the desired structural characteristics. For example, a quasi-isotropic material may include eight layers of material oriented at 0°, +45°, −45°, 90°, 90°, −45°, +45°, 0°. By this, it is meant that the fiber orientation in the first ply is oriented at 0° and serves as a reference layer, the fiber orientation of the second ply is oriented at +45° to the reference, etc. It has also been noted that as cracks form in each ply, the cracks will extend from the top top-to-bottom of each layer and will spread in a direction parallel to the fiber orientation.

This invention, therefore, is in a method of inspecting a composite material on a ply-to-ply basis by positioning an ultrasonic transmitter in acoustical coupling with one surface of the material and by directing a beam of acoustical energy into the material with the axis of the acoustical beam essentially perpendicular to the orientation of the fibers within the ply being inspected. The angle of incidence of the beam with respect to the surface normal of the material is always less than the second critical angle (the critical angle for the transverse wave) for that material and greater than perpendicular to the material surface. For example, it has been found that an angle of incidence with respect to the vertical of 10° to 60° preferred for fiber reinforced polymers and 10° to 35° for metallic composites.

Acoustic energy is reflected from discontinuities within the material, and therefore a crack which extends essentially vertically (or normal to the surface of the material) can be detected only if the angle of incidence of the incoming acoustical beam provides sufficient energy to the crack that the backscattered energy can be detected by an ultrasonic receiver acoustically coupled to the material.

Further, the orientation of the fibers within each layer or ply can be determined by causing relative rotation of the material with respect to the transmitting and receiving transducers (either by rotating the transducers or the material). When using this method, the transmitter and the receiver are positioned at equal angles on either side of a line perpendicular to the orientation of the fibers. Once the fiber orientation is determined, then moving the material with respect to the transducers in a raster fashion will provide information regarding fiber overlap, wavyness, resin-rich areas, and other characteristics of the material.

This technique is not limited to continuously reinforced materials, but can also be used in connection with chopped or whisker reinforced composite materials and so-called sheet molding compounds.

Other objects and advantages of the invention will be apparent from the following description, the accompanying drawings and the appended claims.

DESCRIPTION OF THE DRAWINGS

FIG. 1 is a perspective view showing an ultrasonic transducer engaging the surface of an eight-ply composite material with the transducer being moved with respect to the material in a raster pattern. Representative flaws are shown within the several plys forming the material.

FIG. 2 is a cross-sectional view taken along line 2—2 in FIG. 1.

FIG. 7 is a visual representation of the location and extent of flaws found within one ply of the material wherein the orientation of the fibers within that ply is essentially 90°.

FIG. 8 is a visual representation of the location and length of a plurality of flaws contained in a ply wherein the fibers are orientated at 45°.

FIGS. 9a–9c are visual representations of a polar C-scan using the method illustrated in FIG. 6. FIG. 9a represents a scan of a uniaxial specimen; FIG. 9b represents a scan of a cross-plied specimen; and FIG. 9c represents a scan of a quasi-isotropic specimen.

DESCRIPTION OF THE PREFERRED EMBODIMENT

Figure 3:
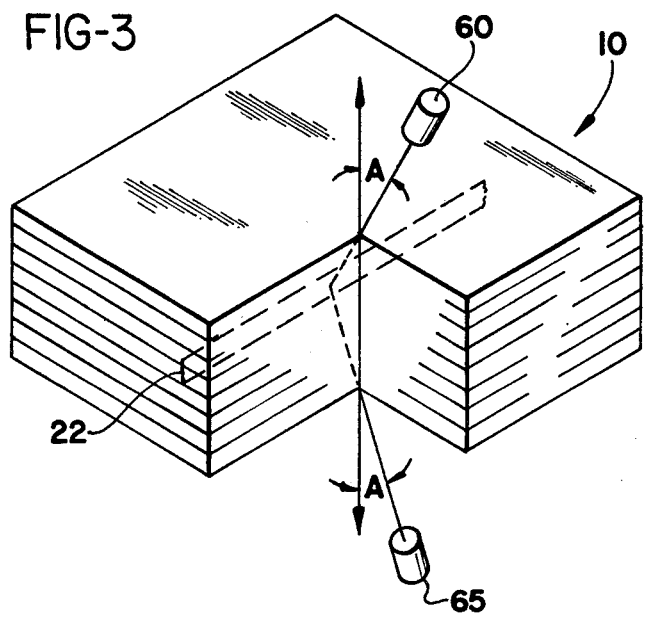
FIG. 3 is a perspective view of a composite material illustrating a method of inspection wherein the transmitting transducer is located on one side of the material and the receiving transducer is placed on the other side of the material and wherein both transmitting and receiving transducers are oriented with the beam essentially perpendicular to the lay of the fiber within the ply being inspected.

Referring now to the drawings which illustrate a preferred embodiment of the invention, a typical section of a composite structure is shown generally at 10 and includes a plurality of layers or plys 12–19, each of which is a fiber reinforced polymer. All of the reinforcing fibers within each ply are aligned in a single direction, and for quasi-isotropic materials, the plys are oriented so that the composite material will exhibit the desired characteristics. For example, in the specimen shown in FIG. 1, eight plys are shown, and the fibers in plys 12 and 19 are oriented at 0°, the fibers in plys 15 and 16 are oriented at 90°, the fibers in plys 13 and 18 are oriented at +45°, and the fibers in plys 14 and 17 are oriented at −45°.

For illustration purposes, several cracks are illustrated in the sample of FIG. 1. The crack generally indicated at 20 is in ply 13 and will extend at 45°, or parallel to the orientation of the fibers making up that specific ply. Similarly, crack 22 in layer 15 extends at 90°, and crack 24 in layer 14 extends at an angle of −45°. Generally, the cracks extend vertically from one surface of the ply to the other, but except for catastrophic failures, cracks generally do not extend from one ply through another ply because of the reinforcing fibers.

Because the cracks generally are vertically oriented, the prior art technique of scanning composite material ultrasonically with a transducer oriented normal to the surface of the material was ineffective because the ultrasonic beam would pass parallel to the surface of the crack and no energy would be reflected or scattered. In the present invention, on the other hand, a transducer 30 is placed at an angle with A (FIG. 2) with respect to surface normal, and because of this, some energy will be reflected off of the surface of the crack, and thus the crack may be detected.

In the preferred embodiment of the invention, the angle A is therefore greater than zero with the normal to the surface, and should be less than the second critical angle of the material. This critical angle will vary from material to material and will even vary with respect to the orientation of the transducer with respect to the reinforcing fibers within the material. Where the material is a graphite/epoxy composite, the angle A is generally between 10° and 50° with a 20° angle being preferred.

The transducer 30 may be moved in a raster fashion over the surface of the material 10 in a pattern shown generally at 40 in FIG. 1.

In FIG. 1, a single transducer 30 is illustrated which serves as both the transmitter and receiving transducers, and may be moved by means of a translating mechanism 50, and an image of the crack can be obtained because of the rastering pattern of C-scanning which is commonly used in standard ultrasonic inspection practices. Information concerning the orientation and the depth of the flaw may be obtained by time-gating the signals from specific depths or plys within the material and also be orienting the transducer perpendicular to the fibers in a specific layer or ply of interest.

Since only cracks in a ply oriented normal to the incident ultrasonic pulses reflect energy back into the receiving transducer, a ply-by-ply interrogation of the material is therefore possible. Therefore, even though the raster pattern 40 shown in FIG. 1 may be followed as each of the ply within the material is scanned, the orientation of the transducer 30 will be modified so that the ultrasonic beam has its axis essentially normal to the orientation of the fibers in the ply of interest. Accordingly, the transducer will be reoriented several times in order to scan completely a specific composite structure.

FIGS. 7 and 8 illustrate a visual image of the cracks found in a ¾-inch by 3-inch specimen which was scanned according to the method described above. FIG. 7 is a representation of the cracks found in plys 15 and 16 which are oriented at 90°. Since both the plys have the same fiber orientation, both would be scanned simultaneously. FIG. 8, on the other hand, shows the cracks which have developed in ply 13 which is oriented at +45°. It will be seen from these illustrations that the cracks start at the edge and work into the ply, and, therefore, both the length of the crack and its position is illustrated along with the density of the cracks within the specimen.

Figure 4:
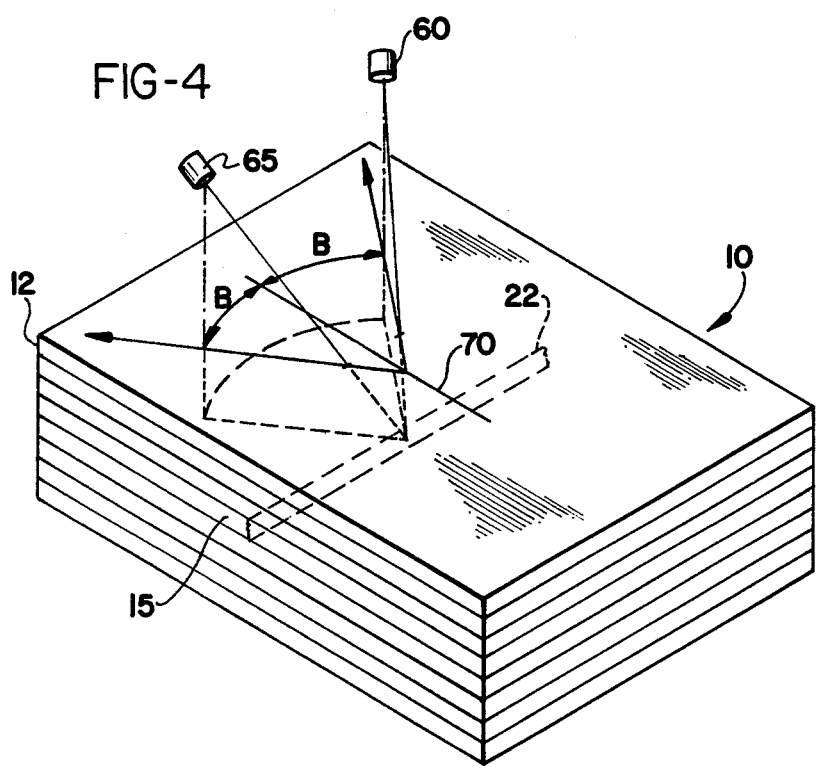
FIG. 4 is a perspective view illustrating the placement of the transmitting and receiving transducers on the same side of the material with the axis of the transducers aligned at equal angles on either side of the line which is perpendicular to the lay of the fibers within the ply being inspected.
Figure 5:
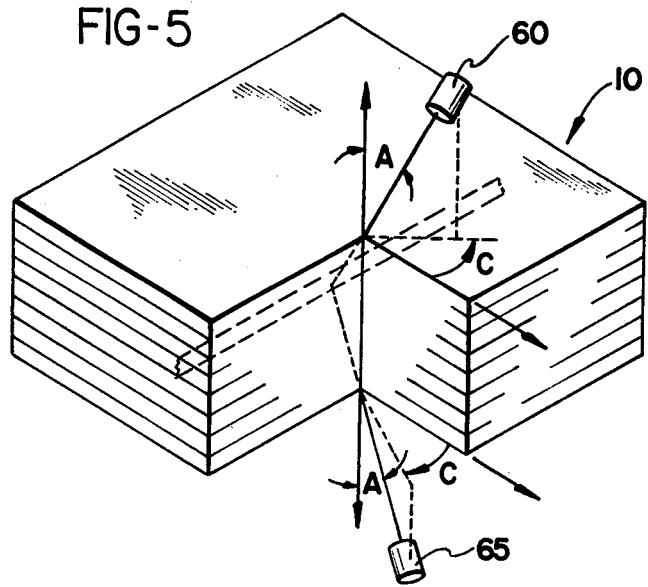
FIG. 5 is a perspective view illustrating the placement of a transmitting transducer on one side of the material, the receiving transducer on the other side of the material, and wherein the transmitter and receiving transducers are located at equal angles on either side of a line which is perpendicular to the lay of the fibers within the ply being inspected.

In FIG. 1, the transmitting and receiving transducers are located on the same axis; however, other methods of collecting reflected energy are possible, and some of these are shown in FIGS. 3–5. In FIG. 3, the transmitting transducer 60 is located on one side of the material 10, and the receiving transducer 65 is placed in a complementary position on the other side of the material. In other words, both transducers are oriented at angle A with respect to surface normal, and both are positioned so that their respective axis are perpendicular to the lay of the fibers (or to the crack 22). This technique has the advantage of minimizing the effect of surface roughness scattering, but it requires that the two transducers be maintained in proper alignment during the scanning process.

FIG. 4 illustrates the positioning of both the transmitting and receiving transducers 60, 65 on the same side of the material 10, but aligned at equal angles B on either side of a line 70 which is perpendicular to the orientation or lay of the fibers within the ply being inspected.

In FIG. 5, the transmitting transducer 60 is located on one side of the material 10 and oriented at an angle C with respect to a line normal to the lay of the fibers and inclined at angle A with respect to surface normal, and the receiving transducer 65 is positioned on the opposite side of the material at the same angle of incidence A and at an equal angle C on the other side of a line normal to the lay of the fibers.

Since the backscattering method described herein is capable of imaging aligned discontinuities in the composite material, it is also possible to image fiber bundles within each ply. If the angle of incidence A is kept constant, and the transducers are rotated about a surface normal, then a maximum in backscatter energy will occur for each unique ply orientation within the composite.

Figure 6:
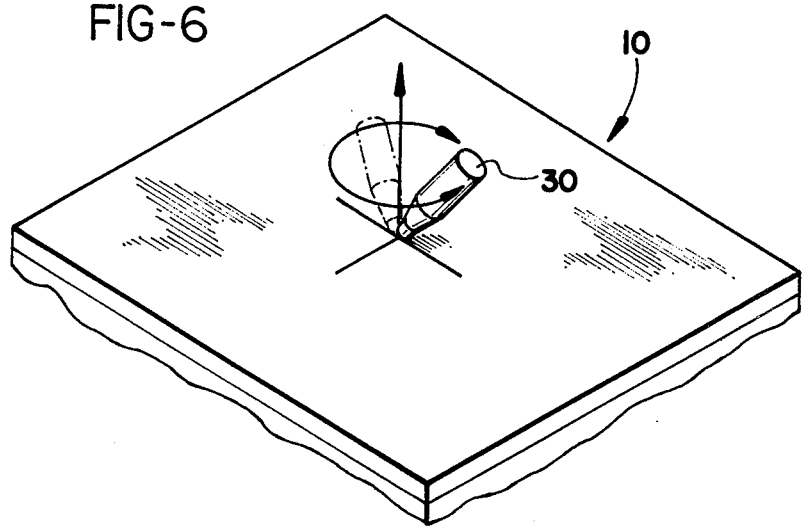
FIG. 6 is a perspective view illustrating a method whereby a transducer is precessed around an axis normal to the surface of the material so that the orientation of the fibers within a specific ply may be determined.

An arrangement for accomplishing this method is illustrated in FIG. 6 where transducer 30 is precessed around a line perpendicular to the surface of the material. Of course, the transducer arrangements of FIGS. 3-5 could also be used. A visual representation of the results of the method illustrated by FIG. 6 are shown in FIGS. 9a-9c. These figures are photographs of polar C-scans wherein FIG. 9a illustrates the results of scanning a uniaxial specimen, that is, wherein all of the fibers within the specimen are aligned so that angle A equal 0°. FIG. 9b shows the results of scanning a cross-plied specimen, and in this case, the angle A for the fibers within the specimen are at 0° and 90°. In FIG. 9c, a quasi-isotropic specimen was scanned, and it may be seen that the fibers are aligned at 0°, +45°, 90° and −45°. In this manner, ply orientations can be determined after the composite 10 is fabricated in order to check for misalignment errors.

Figure 10:
FIG. 10 is a visual representation of a C-scan image of a single ply of a specimen showing wavyness in the fibers embeded within the specimen.

At a particular maximum of reflected energy, if the transducer is then rastered across the specimen, then the fiber bundles in a ply can be imaged and checked for overlap, wavyness, resin-rich areas, etc. FIG. 10 illustrates a C-scan image of a single ply of a graphite/epoxy composite using the apparatus shown in FIG. 1. Wavyness in the fibers within the specimen is obvious.

Indeed, the method described herein will permit for the detection and imaging of many microstructural features within composite materials. It should be noted that the invention is not limited to inspection of materials containing continuous reinforcing fibers, but can also be used where chopped or whisker reinforced composites are employed and so-called sheet molding compounds, that is, in those materials where oriented features of the microstructure are of importance to design, use, or other characterization considerations.

While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

What is claimed is:

1. Method of ultrasonically inspecting composite materials having a plurality of fiber reinforced plys comprising the steps of:

positioning an ultrasonic transmitter in acoustical contact with one surface of the material undergoing test and directing a beam of acoustic energy into the material with the axis of the beam orientated at a preselected angle with respect to the lay of the fibers within the ply of the material being inspected and with angle of incidence of the beam with respect to the surface less than the second critical angle for the material, and positioning an ultrasonic receiver in acoustical coupling with the material at a location for receiving the reflected energy from within the ply of the material being inspected.

2. The method of claim 1 wherein the angle of incidence is between 10° and 60° where the material being inspected is a fiber reinforced polymer.

3. The method of claim 1 wherein the angle of incidence is between 10° and 35° where the material being inspected is a metallic composite.

4. The method of claim 1 wherein the axis of said beam is orientated perpendicular to the lay of the fibers within the ply being inspected.

5. The method of claim 1 wherein said transmitter and said receiver are aligned at equal angles on either side of a line which is perpendicular to the lay of the fibers within the ply being inspected.

6. The method of claim 4 wherein said ultrasonic transmitter and said ultrasonic receiver are located on the same axis.

7. The method of either claims 4 or 5 wherein said ultrasonic receiver is positioned on the same side of the material as the ultrasonic transmitter.

8. The method of either claims 4 or 5 wherein said ultrasonic receiver is located on the side opposite the material from said transmitter.

9. The method of claim 1 further comprising the steps of rotating said transmitter and receiver together around an axis normal to the surface of the material and analyzing the reflected energy to determine the orientation of the fibers within each of the plys comprising the material.

10. The method of claim 1 further comprising the steps of moving said transmitter and receiver together in a raster pattern with respect to the material, and analyzing the reflected energy to determine the presence of flaws within the material.

11. The method of claim 1 further comprising the steps of moving said transmitter and receiver together in a raster pattern parallel to the lay of the fibers within a selected ply and analyzing the reflected energy to determine the characteristics of the ply.

12. Method of ultrasonically inspecting composite materials formed from a plurality of fiber reinforced plys comprising the steps of:

positioning an ultrasonic transmitter in acoustical contact with one surface of the material undergoing test;

positioning the transmitter to direct a beam of acoustic energy into the material with the axis of the beam orientated essentially perpendicular with respect to the lay of the fibers within the ply of the material being inspected and with angle of incidence of the beam with respect to the surface less than the second critical angle for the material;

positioning an ultrasonic receiver in acoustical coupling with the material at a location for receiving the reflected energy from within the ply of the material being inspected;

moving the transmitter and receiver together in a raster pattern across the surface of the material; and inspecting and analyzing the reflected signals with respect to time to determine the presence of flaws within each ply of the material.

13. The method of claim 12 further comprising the step of visually displaying a representation of the reflected signals for each of the plys within the material.

* * * * *

UNITED STATES PATENT AND TRADEMARK OFFICE
CERTIFICATE OF CORRECTION

PATENT NO. : 4,457,174
DATED : July 3, 1984
INVENTOR(S) : Yoseph Bar-Cohen, Robert L. Crane It is certified that error appears in the above—identified patent and that said Letters Patent is hereby corrected as shown below:

Change the assignee to read "Systems Research Laboratories Inc., Dayton, Ohio and The United States of America as represented by the Secretary of the Air Force, Washington, D.C."

Signed and Sealed this

Twenty-sixth Day of February 1985

[SEAL]

Attest:

DONALD J. QUIGG

Attesting Officer     Acting Commissioner of Patents and Trademarks